(12) United States Patent
Inman et al.

(10) Patent No.: US 9,590,533 B2
(45) Date of Patent: Mar. 7, 2017

(54) PIEZOELECTRIC VIBRATIONAL ENERGY HARVESTER

(71) Applicant: The Regents of The University of Michigan, Ann Arbor, MI (US)

(72) Inventors: Daniel J. Inman, Saline, MI (US); M. Amin Karami, Ann Arbor, MI (US); David J. Bradley, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/763,149

(22) PCT Filed: Jan. 23, 2014

(86) PCT No.: PCT/US2014/012690
§ 371 (c)(1),
(2) Date: Jul. 23, 2015

(87) PCT Pub. No.: WO2014/116794
PCT Pub. Date: Jul. 31, 2014

(65) Prior Publication Data
US 2015/0365018 A1 Dec. 17, 2015

Related U.S. Application Data

(60) Provisional application No. 61/755,605, filed on Jan. 23, 2013.

(51) Int. Cl.
*A61N 1/00* (2006.01)
*H02N 2/18* (2006.01)
(Continued)

(52) U.S. Cl.
CPC .......... *H02N 2/186* (2013.01); *A61N 1/3785* (2013.01); *H01L 41/08* (2013.01); *H01L 41/1136* (2013.01)

(58) Field of Classification Search
CPC ..... H02N 2/186; H01L 41/08; H01L 41/0805; H01L 41/082; H01L 41/083; H01L 41/113; A61N 1/3785
See application file for complete search history.

(56) References Cited

U.S. PATENT DOCUMENTS 5,410,210 A * 4/1995 Sato ...................... H01L 41/047
310/332
5,633,554 A * 5/1997 Kaji .................... H01L 41/0986
310/328
(Continued)

FOREIGN PATENT DOCUMENTS

JP 2011097661 A 5/2011
KR 10-0691796 B1 3/2007
WO WO2012105368 A1 8/2012

OTHER PUBLICATIONS

International Search Report for application No. PCT/US2014/012690, dated Apr. 29, 2014, 3 pages.
(Continued)

*Primary Examiner* — Robert N Wieland
(74) *Attorney, Agent, or Firm* — Reising Ethington P.C.

(57) ABSTRACT

A vibrational energy harvester having a base and a piezoelectric transducer formed from a layer of piezoelectric material and extending between a first end at the base and a second end. At least a portion of the piezoelectric transducer is arranged in a back and forth pattern between the first and second ends. A magnetic component provides a magnetic field within which at least a portion of the piezoelectric transducer operates so that it exhibits nonlinear behavior. A biomedical implantable device using the vibration energy harvester can extract energy from heartbeat waveforms (heartbeats) to thereby power a device within the body.

20 Claims, 7 Drawing Sheets

(51) Int. Cl.
  *H01L 41/113* (2006.01)
  *A61N 1/378* (2006.01)
  *H01L 41/08* (2006.01)

(56) References Cited

U.S. PATENT DOCUMENTS

| | | | |
|---|---|---|---|
| 7,948,153 B1* | 5/2011 | Kellogg | H01L 41/1136 310/329 |
| 2002/0014816 A1* | 2/2002 | Takeuchi | B81B 3/0021 310/358 |
| 2006/0217776 A1 | 9/2006 | White et al. | |
| 2007/0276444 A1 | 11/2007 | Gelbart et al. | |
| 2010/0171394 A1* | 7/2010 | Glenn | A61N 1/372 310/339 |
| 2011/0048133 A1 | 3/2011 | Lin et al. | |
| 2011/0095648 A1 | 4/2011 | Zhang | |
| 2011/0215590 A1 | 9/2011 | Arnold et al. | |
| 2012/0267982 A1* | 10/2012 | Carman | H02N 2/186 310/318 |
| 2012/0330109 A1 | 12/2012 | Tran | |
| 2013/0226260 A1* | 8/2013 | Brenner | A61N 1/3785 607/35 |
| 2013/0293069 A1 | 11/2013 | Sakaguchi et al. | |

OTHER PUBLICATIONS

Written Opinion for application No. PCT/US2014/012690, dated Apr. 29, 2014, 6 pages.

Extended European Search Report for application No. EP14743063, dated Aug. 9, 2016, 13 pages.

Berdy, David F., Low-Frequency Meandering Piezoelectric Vibration Energy Harvester, IEEE Transactions on Ultrasonics, Ferroelectrics, and Frequency Control, May 2012, pp. 846-858, vol. 59, No. 5.

* cited by examiner

PIEZOELECTRIC VIBRATIONAL ENERGY HARVESTER

TECHNICAL FIELD

This invention relates generally to structures and methods for harvesting vibrational energy using piezoelectric materials.

BACKGROUND

Energy harvesters for use in operating low power electronics have been an active area of interest for decades. Vibrational energy harvesters may be configured to collect the energy associated with mechanical movement by converting mechanical energy to some other form of energy, such as electrical energy, for immediate use and/or storage for later use. For example, piezoelectric materials can generate an electrical potential when mechanically deformed and can be connected to an electrical load or storage device to harvest energy from mechanical vibrations. Such energy harvesters could be used to operate wireless sensors in remote locations or in other applications where battery replacement is impractical. Energy harvesters could also serve to reduce reliance on batteries, which often include hazardous materials, and reduce the need for electrical wiring in some cases. However, such energy harvesters have not been adopted for widespread use, due in part to certain size, frequency and amplitude constraints that render them unsuitable for many practical applications.

One application for energy harvesters is implantable biomedical devices. Many vibrational energy harvesters that are configured to extract energy from human motion are designed for attachment to the limbs. Where the biomedical device is intended for implant in the torso, it is sometimes preferable to include the energy harvester as part of the device package. One type of energy harvester that can be used in the torso is a microbial fuel cell, which generally relies on the oxidation of glucose to generate power. Another type of energy harvester uses a piezoelectric film wrapped around an artery and is configured to harvest energy from artery expansions. Another type of energy harvester includes piezoelectric ribbons printed onto a rubber substrate and is configured to harvest energy from lung expansion during respiration.

SUMMARY

In accordance with one aspect of the invention, there is provided a vibrational energy harvester, comprising: a base and a piezoelectric transducer comprising a layer of piezoelectric material and extending between a first end at said base and a second end, wherein at least a portion of the piezoelectric transducer is arranged in a back and forth pattern between the first and second ends.

In accordance with another aspect of the invention, there is provided a vibrational energy harvester, comprising a base, a piezoelectric transducer extending from the base, and a magnetic component having an associated magnetic field, wherein at least a portion of the piezoelectric transducer operates within the magnetic field so that the transducer exhibits non-linear behavior.

In accordance with another aspect of the invention, there is provided a method comprising the steps of: providing a piezoelectric transducer having a geometry with an associated power output over a range of input frequencies, and inducing non-linear behavior in the piezoelectric transducer, thereby increasing the power output of the transducer over the range of input frequencies.

In accordance with another aspect of the invention, there is provided an implantable biomedical device, comprising a non-linear piezoelectric energy harvester. In at least some embodiments, the energy harvester is responsive to a heartbeat waveform.

In accordance with yet another aspect of the invention, there is provided a wireless monitoring device adapted for attachment to a structure to be monitored, the monitoring device being powered by a piezoelectric energy harvester configured to harvest vibrational energy from the structure and comprising a piezoelectric transducer having a layer of piezoelectric material. The piezoelectric transducer is characterized in that it exhibits non-linear behavior, has at least a portion that is arranged in a back and forth pattern between first and second ends of the transducer, or both.

Embodiments of the invention include all technically-compatible combinations of the various features disclosed herein and in the drawings.

BRIEF DESCRIPTION OF THE DRAWINGS

Preferred exemplary embodiments will hereinafter be described in conjunction with the appended drawings, wherein like designations denote like elements, and wherein.

DESCRIPTION OF THE ILLUSTRATED EMBODIMENTS

As described below, a vibrational energy harvester can be constructed with a piezoelectric transducer having enhanced efficiency and power output, particularly at relatively low frequency excitation, in a compact size and shape. Non-linear behavior may also be induced in the transducer, thereby increasing the frequency range in which it can produce useful amounts of power. One useful application of the energy harvester is as a power source for biomedical implant devices, such as pacemakers, implantable cardio-verter defibrillators (ICDs), or other implantable devices. The energy harvester can be configured to produce sufficient amounts of electrical power to operate and/or continuously recharge the battery in a modern pacemaker, using heartbeat vibrations in the chest area as the vibrational input, potentially eliminating post-implant surgical procedures performed primarily for battery replacement. The energy harvester described herein may also be adapted for use in other applications, such as long-term electronics applications where battery replacement is impractical or impossible.

Figure 1:
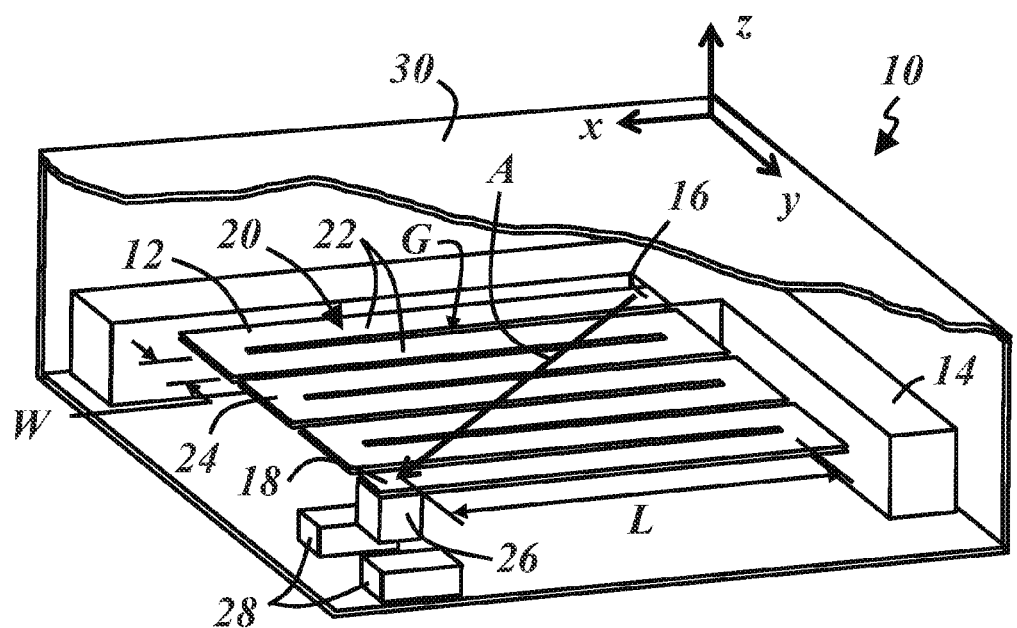
FIG. 1 is a schematic cutaway view of one embodiment of a vibrational energy harvester.

With reference to FIG. 1, there is shown an illustrative vibrational energy harvester 10. The energy harvester 10 is a piezoelectric energy harvester and includes a piezoelectric transducer 12 extending from a base 14. The transducer 12 extends from a first end 16 at the base 14 to a second end 18 away from the base. In this example, the first end 16 is fixed at the base 14 and the second end 18 is a free end. In other examples, the second end 18 may be fixed, and the transducer 12 may include one or more additional free or fixed ends. The transducer 12 may be fixed at the base 14 by any suitable technique, or the transducer may include a portion that is integral or formed together as one piece with the base. The piezoelectric transducer 12 may have a layered structure including at least one layer of piezoelectric material. In one embodiment, the transducer 12 includes a layer of piezoelectric material interposed between two electrode layers. The transducer 12 may also include one or more substrate layers and/or adhesive layers. Any of the layers may be continuous or discontinuous layers, and other piezoelectric transducer structures are possible.

Figure 2:
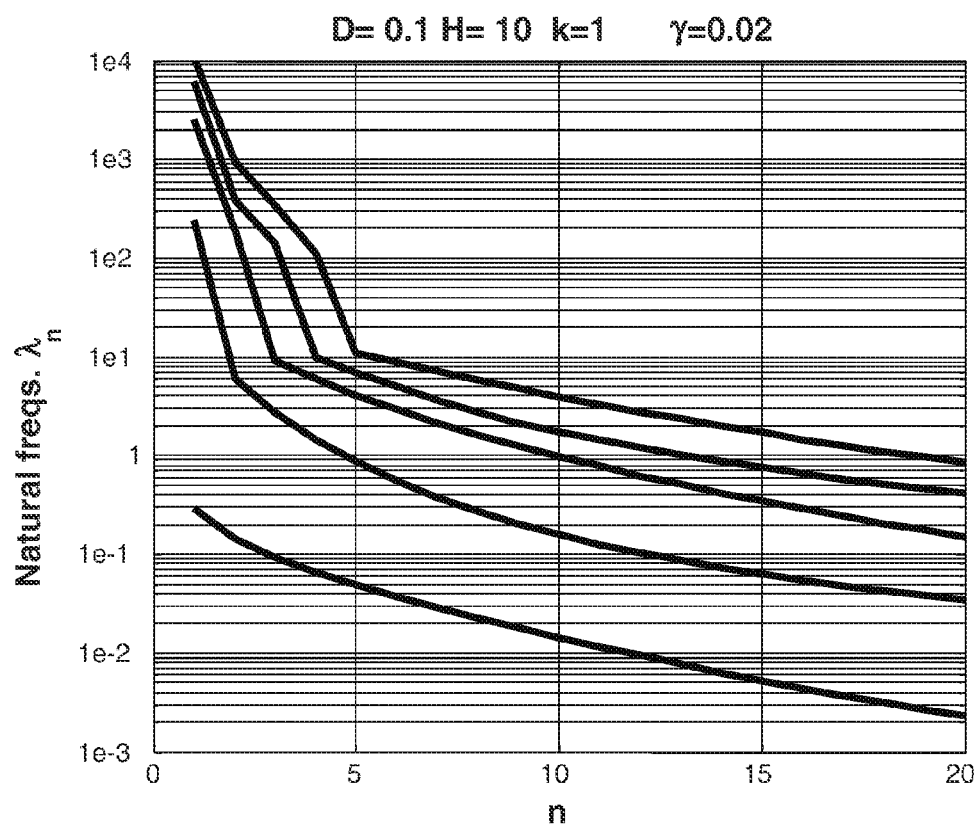
FIG. 2 is a plot showing the effect of the number of back and forth turns in a piezoelectric transducer geometry on the natural frequency of the transducer.

The illustrated transducer 12 is generally planar or flat and is arranged in a back and forth pattern 20 between the first and second ends 16, 18. A back and forth pattern defines a path between two points that is not a straight line. In this context, as the transducer 12 extends away from the first end 16, it does so in a direction that is different from the direction of a straight line A between the first end and the second end 18. In the illustrated example, the transducer 12 extends from the first end 16 in the x-direction and away from the straight line A. To reach the second end 18, the path must at some point change direction so that it extends in a direction back toward the straight line A. The illustrated back and forth pattern 20 forms a path with multiple directional changes between the first and second ends 16, 18 and may be referred to as a zigzag pattern or a serpentine pattern that snakes its way back and forth across the straight line A as it extends between the first and second ends. In some embodiments, only a portion of the piezoelectric transducer is arranged in a back and forth pattern. In some embodiments, one or more portions of the transducer may extend in the same direction as the straight line A between the first and second ends 16, 18. As discussed in greater detail below, the back and forth pattern 20 can be useful to provide the transducer 12 with a relatively low natural frequency in a compact shape for efficient energy harvesting in applications where the dominant (e.g. high amplitude) vibrations are at low frequencies. The chart of FIG. 2 generally shows the effect of the number of back and forth turns in a serpentine or zigzag configuration like that in FIG. 1, with the natural frequency of the transducer decreasing with an increasing number of back and forth turns.

The illustrated transducer 12 may also be described as having a plurality of beams 22, each of which has an associated length L and width W. In this example, the beams 22 are arranged parallel with one another with a gap G defined between adjacent beams. Each beam 22 is connected to any other single adjacent beam at only one end by a connecting portion 24. Beams 22 having two adjacent beams (i.e. located across opposite gaps G on both sides) are connected to one of the two adjacent beams at one end and the other of the two adjacent beams at the opposite end. Other back and forth configurations may include an angled zig-zag pattern, in which alternating beams are parallel, adjacent beams are not parallel, and each beam is connected to an end of an adjacent beam; a spiral pattern; or a combination of patterns.

The energy harvester 10 may also include one or more magnetic components 26, 28 and a housing 30, as shown in FIG. 1. Each of the magnetic components 26, 28 has an associated magnetic field. The magnetic components 26, 28 are arranged so that at least a portion of the transducer 12 operates within one or more of the associated magnetic fields. Operating the transducer 12 in the presence of a magnetic field can induce non-linear behavior in the transducer. For example, deflection in the z-direction of the second end 18 of the transducer may be a linear function of the applied force, or at least have a linear region, in the absence of magnetic components. The magnetic components 26, 28 can alter the force-deflection behavior of a given transducer geometry because the applied magnetic force changes with the relative position of the transducer and the magnetic field(s), thus inducing non-linear behavior. For instance, the magnetic components 26, 28 may have their respective poles arranged so that component 26, affixed at the second end 18 of the transducer 12, is magnetically attracted toward the components 28 affixed to the housing 30 (i.e. the downward direction in FIG. 1). In this case, as the second end 18 of the transducer 12 moves away from the magnetic components 28, the initial deflection may be less than normal for the given transducer geometry, but the reducing effect of the magnetic field diminishes with additional movement.

Alternatively the respective magnetic poles of the magnetic components 26, 28 may be arranged to repel each other with similar inducement of non-linear behavior. In other examples, multiple magnetic components may be arranged with different locations, field strengths, pole arrangements, etc. to customize the non-linear effect. Any of the magnetic components 26 or 28 may be replaced with a ferromagnetic component that operates in the magnetic field of a magnetic component. The movement of ferromagnetic components may be affected by magnetic fields, even though they may not actively contribute to the size, shape, strength, or direction of the field(s). Other examples of magnetic components configurations are described below. Inducing non-linear behavior in the piezoelectric transducer can broaden the range of frequencies at which the transducer produces useful amounts of power. This effect is shown generally in the chart of FIG. 3, where the linear energy harvester exhibits a peak between 7 and 8 Hz, corresponding to a natural frequency of the transducer, and the non-linear harvester exhibits a broadened power band. Other techniques for imparting the transducer 12 with non-linear behavior are possible to achieve the same benefits.

Figure 4:
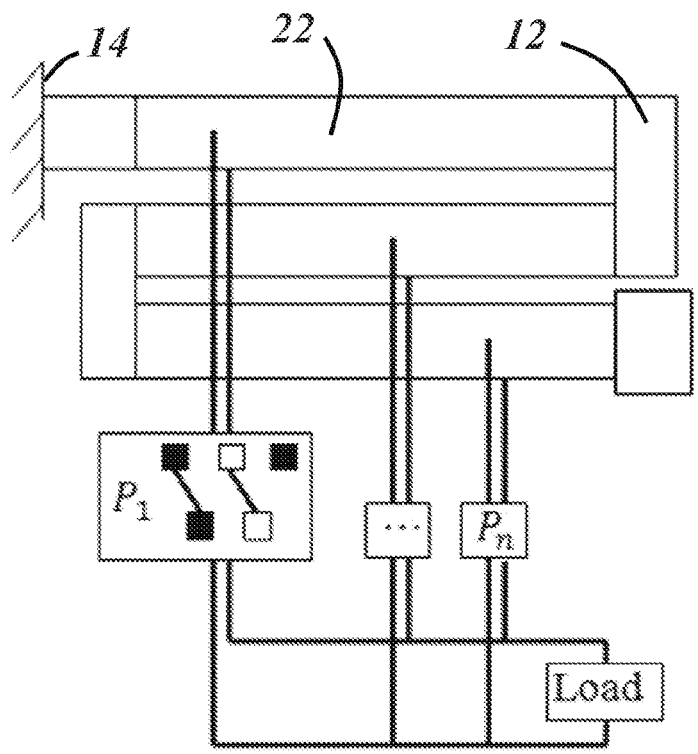
FIG. 4 is a schematic view of another example of the energy harvester, showing electrical connections to a load or storage device.

FIG. 4 is a schematic view of another example of the energy harvester 10, showing electrical connections to a load or storage device. In this example, the individual beams 22 are electrically isolated from one another (i.e., one or more of the transducer layers is discontinuous) and connected to the load in a parallel configuration. Other configurations are possible.

The energy harvester is described below by way of a non-limiting example in the form of a power source for an implantable biomedical device, namely a pacemaker. The power requirement of pacemakers has been significantly reduced over the years, and one microwatt (1.0 µW) is a reasonable upper estimate of the power required by a modern pacemaker. The size of a typical pacemaker is about 42 mm×51 mm×6 mm. In a typical pacemaker, the battery-based power source accounts for about ⅔ of the overall size of the pacemaker. The analyses described below were conducted to target a 50% size reduction for the power source, with 27 mm×27 mm×6 mm as the target maximum size of the energy harvester. The choice of biocompatible materials can be a major issue in designing implantable biomedical devices. The most commonly used piezoelectric materials (PZT) are composed of lead, which is toxic. The batteries and the circuits of the pacemakers are typically encapsulated in a sealed case or housing made from titanium, which is a biocompatible material, to ensure that there is no contact between the interior of the body and the pacemaker batteries or circuits. Another design consideration is that the energy harvester should not impede the heart beating action. Direct attachment of the energy harvester or harvester-containing device to the exterior of the heart can mass load the heart and may be problematic.

Figure 5:
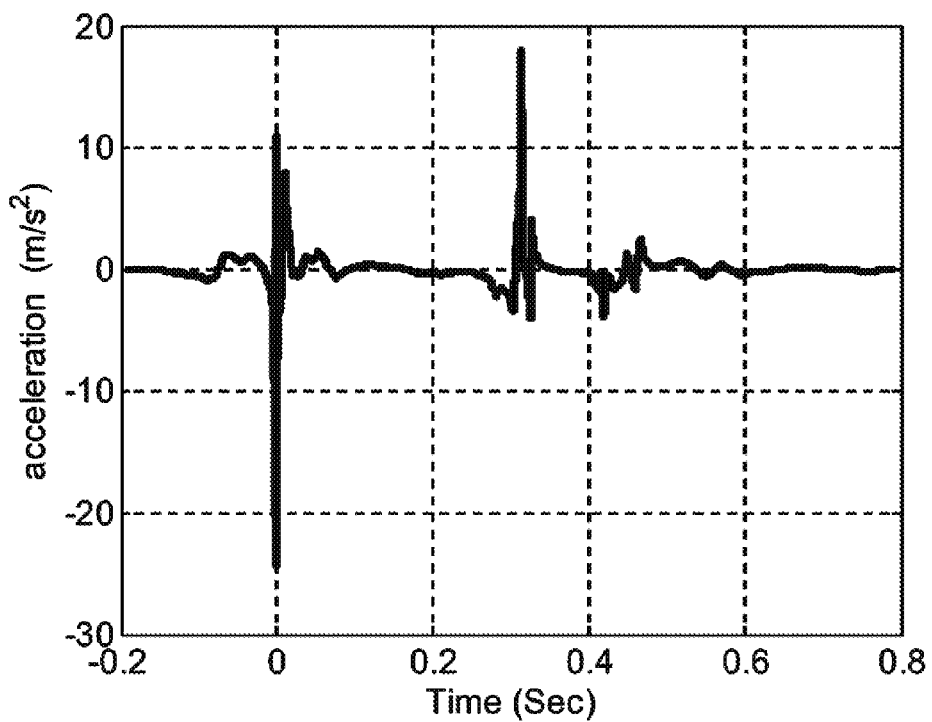
FIG. 5 is a chart showing an example of a heartbeat waveform.

Vibrations in the vicinity of the heart were estimated using ultrasonic velocity measurements, as described by Kanai et al. (IEEE Trans. Ultrason. Ferroelectr. Freq. Control 43, 791 (1996)) and shown in FIG. 5. Kanai measured the velocity of two points on the lower sides of the interventricular septum, which is the wall separating the left and right ventricles of the heart. Since the measurement points are close to the thoracic diaphragm, the velocity data is a safe estimate for the vibration of the part of the body close to heart area.

The behavior of a linear vibrational energy harvester with a piezoelectric transducer having a back and forth arrangement as in FIG. 1 was analyzed (in the absence of the magnetic components). Because the target maximum size of the energy harvester is relatively small, a cantilever beam harvester design has a limited cantilever length, resulting in natural frequencies too high to harvest energy from the heart-regulated frequencies. The back and forth transducer pattern allows construction of a transducer with a much lower natural frequency in the small packaging window. The transducer geometry shown in FIG. 1 may also be referred to as a unimorph zigzag geometry. This geometry can be designed to have a low natural frequency and high strength. The frequency spectrum of heart beat oscillations ranges from fractions of a Hertz to about 50 Hz. For the analysis, the linear energy harvester was configured to harvest vibrational energy primarily from the 39 Hz frequency component of the heartbeat oscillation—the amplitude of the 39 Hz frequency component being relatively high (0.3 ms$^{-2}$). In addition, 39 Hz is a relatively high frequency and results in better power production. The power generated by the zigzag energy harvester operated at resonance is calculated from the model described by Karami et al. ("Parametric study of zigzag microstructure for vibrational energy harvesting," J. Microelectromech. Syst. (2012)). The design procedure is similar to that described by Karami et al. (J. Intell. Mater. Syst. Struct. 22, 271 (2011)), and every aspect of the zigzag energy harvester was optimized for better power generation.

Figure 6:
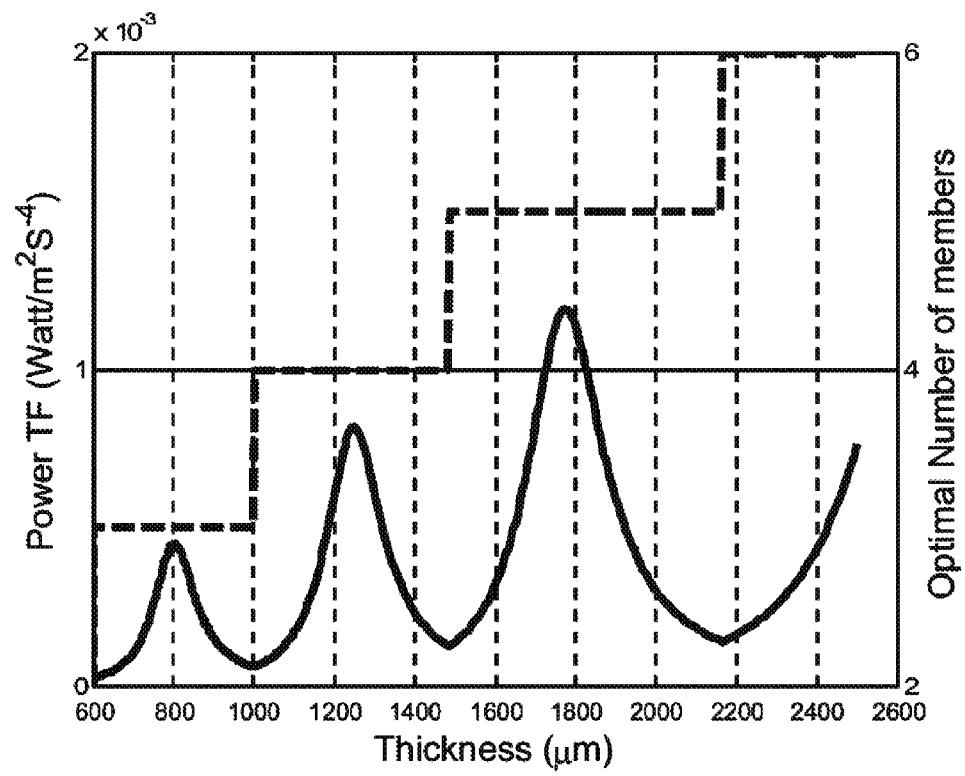
FIGS. 6 and 7 are charts showing the optimal power transfer function and number of piezoelectric beams of a meso-scale transducer and a micro-scale transducer, respectively, as a function of substrate thickness, each transducer having a zigzag structure.

For this first linear energy harvesting analysis, the target maximum harvester size was used, with the zigzag transducer having beams with a length of 27 mm. Brass was used as the substrate material due to its large density and relatively large Young's modulus. The piezoelectric layer was considered to be attached to the substrate using epoxy (polyepoxide) adhesive. The commercially available PZT-5A ceramics selected for the device were 0.01 inches (254 µm) thick. The optimization procedure resulted in the relationship between the power and the substrate thickness shown in FIG. 6, where the maximum power corresponds to a substrate thickness of about 1800 µm. The power output from such a structure is about 10 µW. Thus, a linear meso-scale energy harvester sized and configured as described can therefore generate about 10 times the power requirement (1.0 µW) of a modern pacemaker if excited at nominal heart rate. The power output is very sensitive to heart rate, however. Non-linear behavior, described further below, may be induced in the energy harvester to help overcome heart rate sensitivity.

Figure 7:
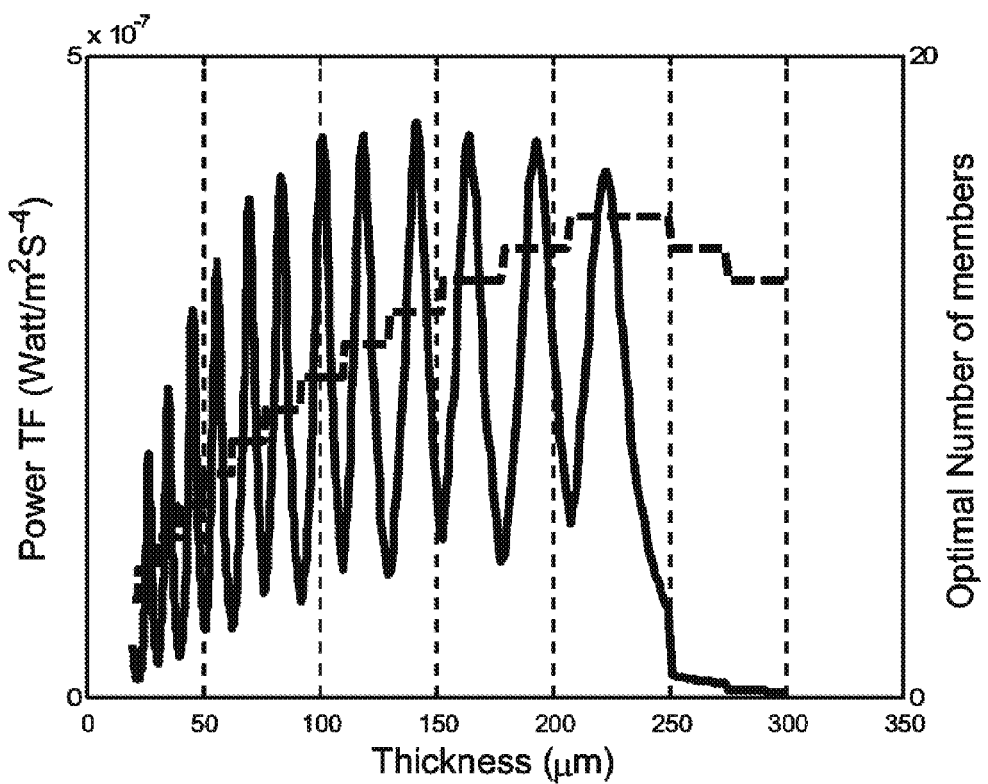

A similar design and optimization procedure was conducted for a micro-scale energy harvester having a length of only 5 mm. The thickness of the piezoelectric layer may be somewhat limited in micro-scale devices, which can significantly affect the power output. The optimization analysis, shown in FIG. 7, indicates that, with the thickness of the piezoelectric layer is limited to 3 µm, the optimized energy harvester power output is only about 39 nW.

Figure 8:
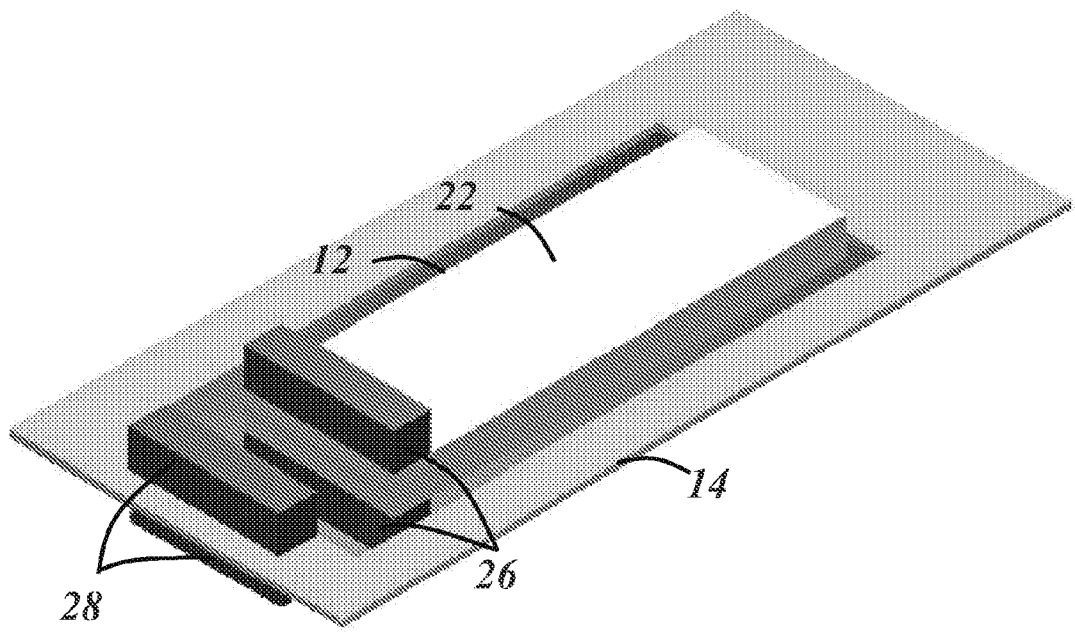
FIG. 8 is a schematic view of an illustrative non-linear energy harvester.

One example of a non-linear energy harvester is illustrated in FIG. 8. The beam 22 of the transducer 12 is a bimorph and has a brass substrate. The repelling force between the magnets 26 at the free end 18 of the beam and the magnets 28 attached to the body 14 opposes the elastic restoring force of the composite beam. Since the magnetic force is a nonlinear function of the beam tip displacement, the magnets 26, 28 make the energy harvesting system nonlinear. The repelling force can also fundamentally change the dynamics of the system. For example, when the repulsive magnetic force between the tip and base magnets overcomes the restoring elastic force, the zero deflection position becomes unstable. Thus, in the configuration shown, there are two equilibrium positions for the beam on the two opposite sides of center. A system with two equilibrium positions may be referred to as a bi-stable system.

Figure 3:
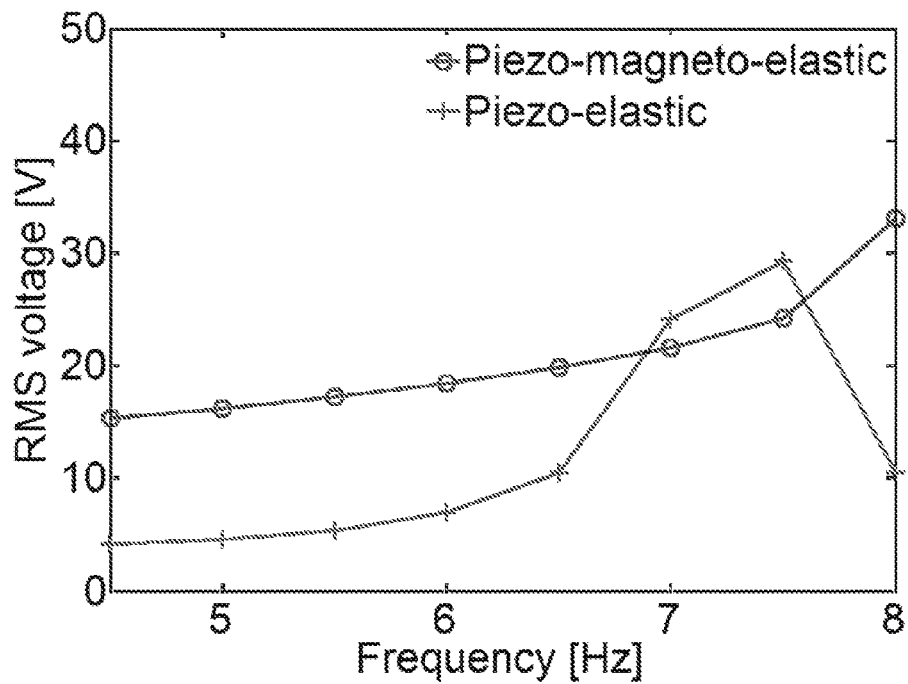
FIG. 3 is a plot showing the effect of non-linear behavior on energy harvester frequency response.

As previously indicated in FIG. 3, a non-linear energy harvester exhibits a larger frequency bandwidth than a linear harvester. Thus, inducing or otherwise implementing non-linearity into an energy harvester designed to harvest energy from heartbeat vibrations can be made relatively insensitive to heart rate. The illustrative bimorph beams are 27 mm×27 mm. The dimensions of the illustrative base and tip magnets are 25.4 mm×3.18 mm×3.18 mm. The residual flux densities of the magnets were derived during the optimization. To estimate the magnetic repulsive force between the two magnets, the approach described by Stanton et al. (Physica D 239(10), 640 (2010)) was used.

Figure 9:
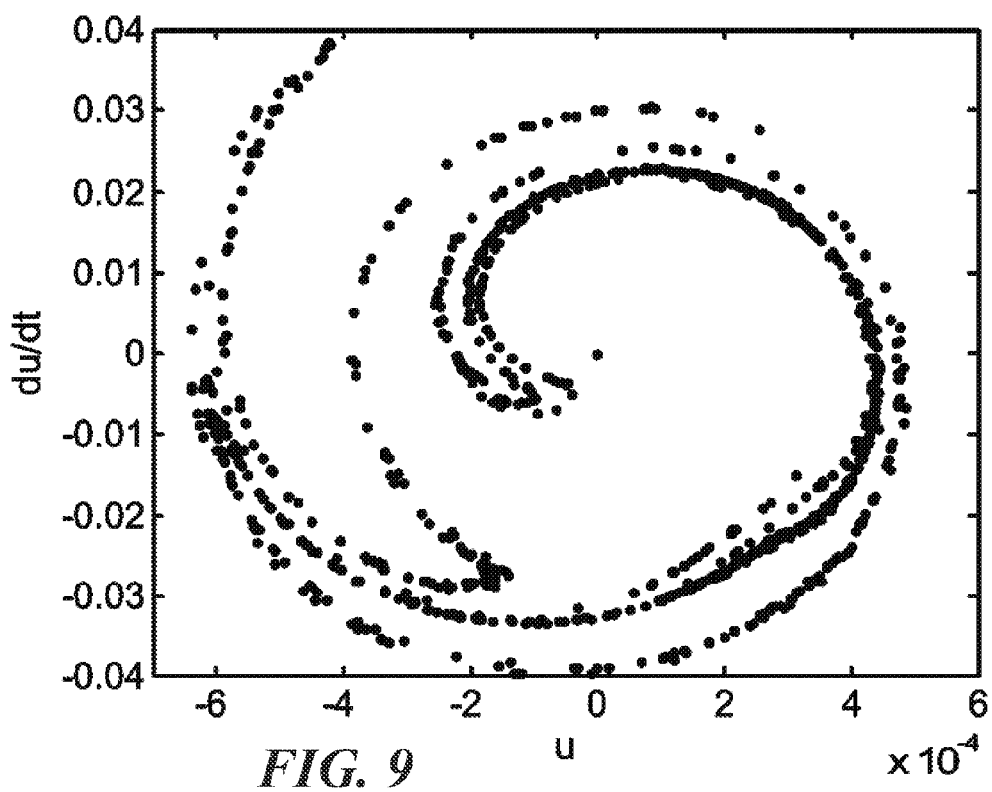
FIG. 9 is a chart showing the strange attractor of the chaos in response to a heartbeat waveform.

The response of a non-linear Duffing system to a heartbeat waveform is described below. Although heartbeat vibrations are periodic, the response of an energy harvester can be fundamentally different from the response of the harvester to a harmonic excitation. For instance, an optimized mono-stable device (i.e., a device having only one equilibrium position), where the brass substrate is 25 µm thick and the thickness of each of the piezoelectric layers is 200 µm, undergoes chaotic vibration in response to the periodic (but not harmonic) heartbeat waveform. While chaotic vibration of mono-stable systems in response to harmonic input is possible, it is uncommon. The strange attractor of the chaotic motion of the harvester is illustrated in FIG. 9.

Figure 10:
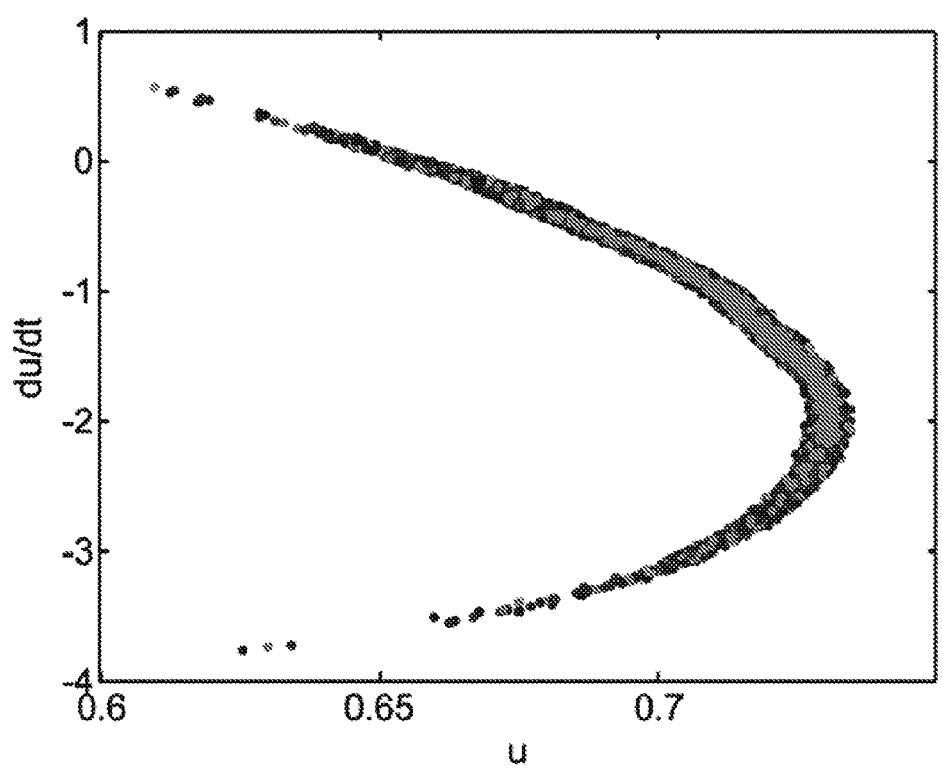
FIGS. 10 and 11 are Poincare' maps of a bi-stable harvester in response to heartbeat oscillations at normal intensity and in response to heartbeat oscillations at 10 times normal intensity, respectively.
Figure 11:
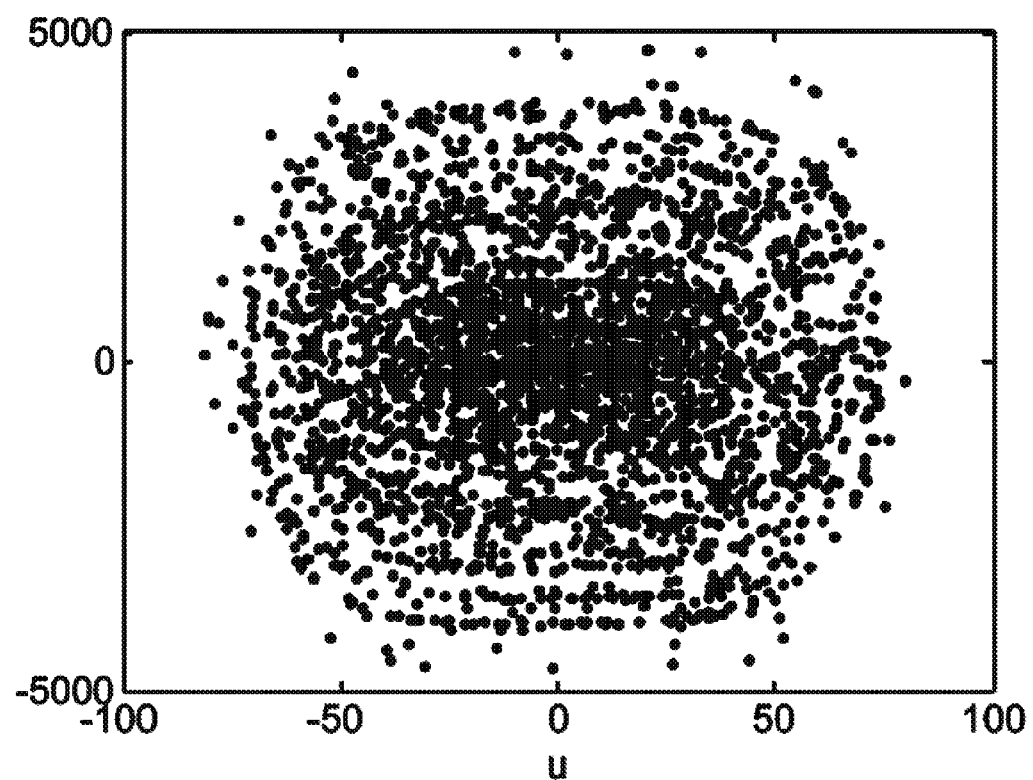

Analysis shows that, compared to a mono-stable harvester, a bi-stable harvester is superior both in terms of power level and heart rate insensitivity. Therefore the focus of the description below is on a bi-stable energy harvester. The single mode non-dimensional equations of motion of the bi-stable device are:

$$\frac{d^2 y}{d\tau^2} + 2\zeta\frac{dy}{d\tau} - \frac{1}{2}y + \phi V = f(\tau)$$

and $$\frac{dV}{d\tau} + \alpha V = \beta\frac{dy}{d\tau},$$

where y is the modal coordinate, $\tau$ is the dimensionless time, $\zeta$ is the modal damping ratio, $\phi$ and $\beta$ are the piezoelectric coupling coefficients, V is the voltage across the load, a is related to the time constant of the electrical system, and f is related to the heart beat excitations.

Where the amplitude of the excitation is only 1/10 of the typical heartbeat vibrations, the bi-stable system exhibits small amplitude periodic motion. This is qualitatively similar to the response of the system to harmonic oscillations. Where the bi-stable harvester is excited by the heartbeat wave form, it exhibits intra-well chaos, as shown in FIG. 10. The main distinction between intra-well chaos and ordinary chaos in Duffing systems is that, in the former, the tip remains in the vicinity of one of the equilibrium positions. Although this has been observed in the response of bi-stable harvesters to harmonic input, its occurrence is a rare phenomenon. In contrast, when the base excitations have the form of heartbeat accelerations, intra-well chaos commonly occurs. Extreme heartbeats (e.g., about 10 times more intense than normal beats) induce chaotic motion of the energy harvester, as indicated in FIG. 11.

A non-linear bi-stable energy harvester was analyzed and optimized, based on its response to the heart beat waveform. The thickness of the substrate was assumed to be 100 µm. For each value of the thickness of the piezoelectric layer, the residual magnetic flux density and the magnetic gap were optimized. The power output of the harvester was evaluated based on numerical integration of the above-mentioned governing equations. To evaluate the power, the system was ran for numerous periods and allowed to reach steady state. The power output was averaged over a few excitation periods to give the power metric.

Figure 12:
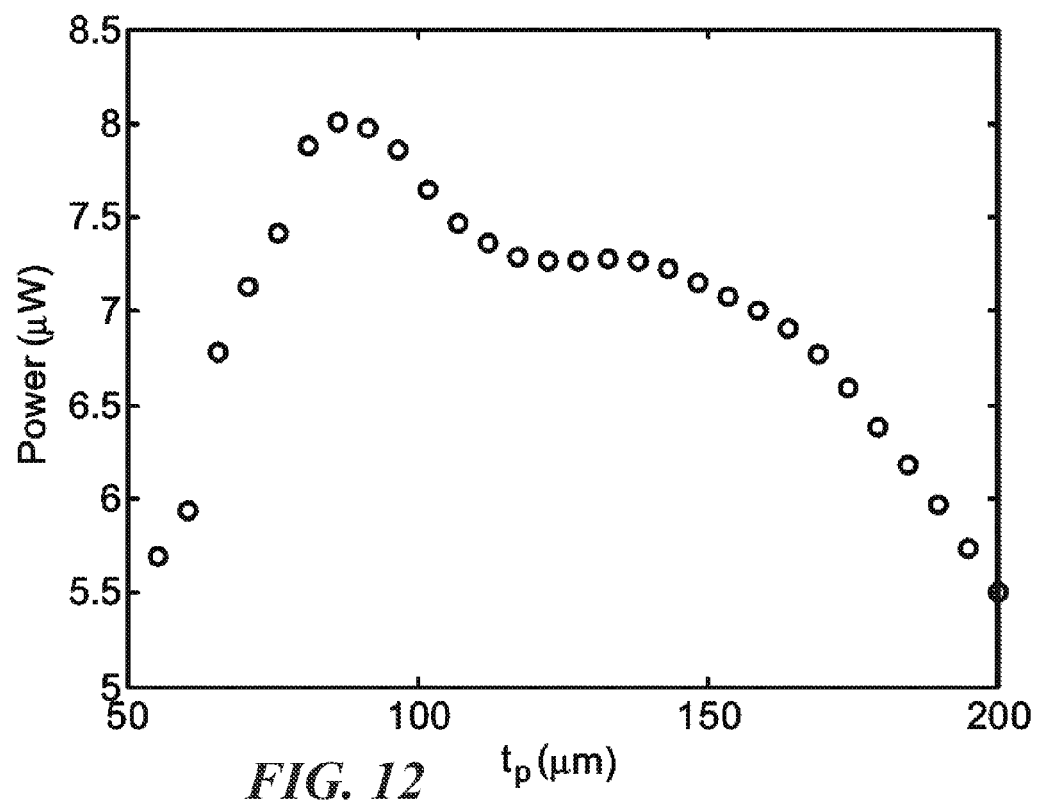
FIG. 12 is a chart showing the power output of a non-linear bi-stable energy harvester, as a function of piezoelectric layer thickness.
Figure 13:
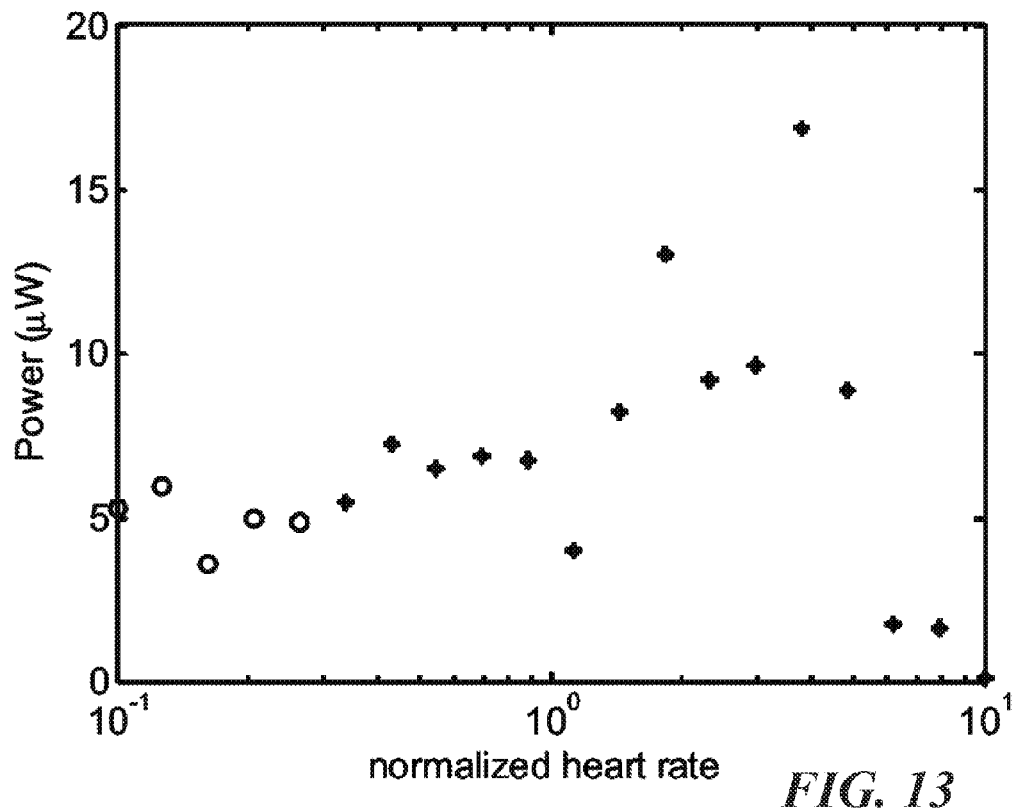
FIG. 13 is a chart showing the power output of a bi-stable energy harvester, as a function of heart rate.

Data points in the charts of FIGS. 12 and 13 are plotted as circles if the response of the energy harvester was periodic, or as stars if the response was chaotic. FIG. 12 illustrates the variation of the power output with the thickness of the piezoelectric layer. It also shows that a non-linear hybrid energy harvester with an 80 µm piezoelectric layer thickness can generate about 8 µW from the heartbeat oscillations. This amount of power is about eight times the power requirement of modern pacemakers.

To evaluate the frequency sensitivity of the bi-stable hybrid device, the relationship between the power output of the optimal design and the heart rate was analyzed. As indicated in FIG. 13, although both the type of vibrations and the output power change with the heart rate, the bi-stable energy harvester always generates more than 3 µW of power. It is also notable that the range of heart rates considered, and shown in FIG. 13, spanned two orders of magnitude, ranging from 7 beats per minute to 700 beat per minute, making the performance of the harvester satisfactory over the entire range of typical human heart rates.

Figure 14:
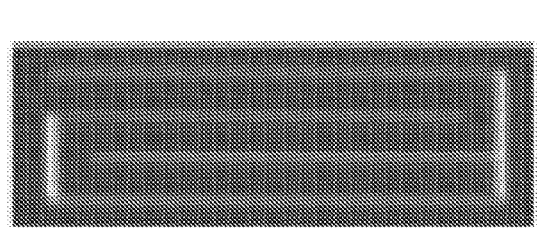
FIGS. 14 and 15 are photographic images showing examples of micro-scale and macro-scale transducer geometries.
Figure 14:
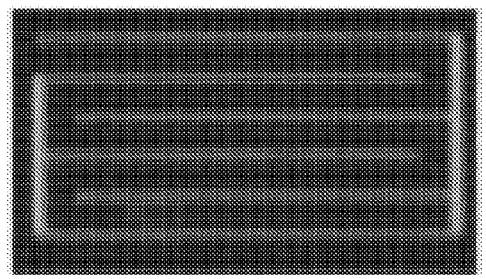
Figure 15:
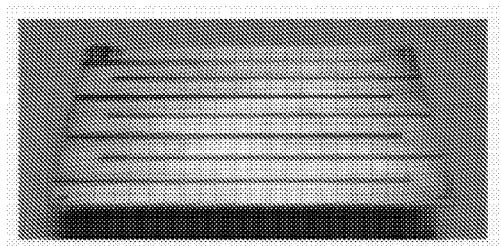
Figure 15:
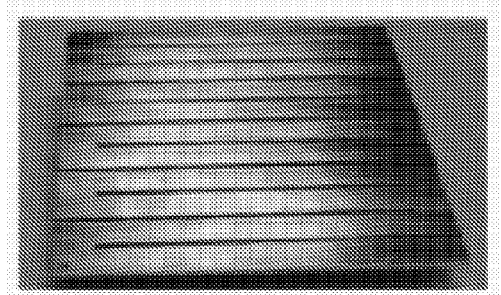

The above analysis relative to heartbeat-excited energy harvesters for use as a pacemaker power source is only one example of useful applications of the energy harvester taught herein. As is apparent from the above description, various combinations of piezoelectric transduction, magnetic fields and transducer geometries can provide a vibration-based harvesting device that is scalable in size, frequency range and amplitude to fit a variety of applications. A static magnetic field may be used to induce non-linear behavior in the transducer. Additionally or alternatively, a zigzag and/or serpentine pattern may be employed in the transducer geometry. The energy harvester can be scaled to from a relatively small MEMs-scale to a larger macro-scale and can produce energy from a wide range of ambient vibration in terms of frequency and amplitude. A photographic image of exemplary MEMs-scale transducer patterns is shown in FIG. 14, where the length scale is about 1 mm, and a photographic image of exemplary macro-scale transducer patterns is shown in FIG. 15, where the length scale is about 10 cm.

As such the energy harvester described here represents an enabling technology that can allow the monitoring of certain tasks or conditions not possible before. For example, the energy harvester may be integrated with and/or employed to power a wireless monitoring device and attached to a structure to be monitored. The monitoring device can be powered by the piezoelectric energy harvester, which can be configured to harvest vibrational energy from the structure. Some non-limiting examples include devices for monitoring components of manned or unmanned aircraft, devices for monitoring bridges, pipelines, or buildings, devices for monitoring turbine engine components, and devices for monitoring various conditions of an automobile, such as tire pressure.

In addition to pacemakers and ICDs, other medical applications include implantable drug therapy devices, power generation patches that could be fitted to existing pacemakers, neurostimulation devices, deep brain stimulation devices, and contractility diagnostic sensors, to name a few.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A vibrational energy harvester, comprising:
   a base; and
   a piezoelectric transducer comprising a layer of piezoelectric material and extending between a first end at said base and a second end, wherein at least a portion of the piezoelectric transducer is configured to undergo mechanical strain in response to movement of the energy harvester and is arranged in a back and forth pattern between the first and second ends.

2. A vibrational energy harvester as defined in claim 1, wherein the second end is a free end that moves with respect to the base in response to movement of the energy harvester.

3. A vibrational energy harvester as defined in claim 1, wherein at least a portion of the layer of piezoelectric material is arranged in the back and forth pattern.

4. A vibrational energy harvester as defined in claim 1, wherein the piezoelectric transducer is configured to have a characteristic force-deflection behavior in the absence of a magnetic field, the energy harvester further comprising a magnetic component having an associated magnetic field and being arranged so that a linear portion of said characteristic force-deflection behavior is rendered non-linear.

5. A vibrational energy harvester as defined in claim 1, wherein the piezoelectric transducer has a unimorph zigzag geometry comprising a plurality of beams arranged parallel with one another with a gap defined between adjacent beams, each one of the beams being connected to an adjacent one of the beams by a connecting portion located at an end of each of the connected beams.

6. A vibrational energy harvester as defined in claim 1, wherein the piezoelectric transducer comprises a bimorph beam.

7. A vibrational energy harvester as defined in claim 1, wherein the energy harvester is a bi-stable energy harvester.

8. A vibrational energy harvester, comprising:
   a base;
   a piezoelectric transducer extending from the base; and
   a magnetic component having an associated magnetic field, wherein at least a portion of the piezoelectric transducer operates within the magnetic field so that the transducer exhibits non-linear force-deflection behavior.

9. A vibrational energy harvester as defined in claim 8, wherein the piezoelectric transducer comprises a cantilever beam extending from the base to a free end.

10. A vibrational energy harvester as defined in claim 8, wherein the piezoelectric transducer comprises a bimorph beam.

11. A vibrational energy harvester as defined in claim 8, wherein the energy harvester is a bi-stable energy harvester.

12. A vibrational energy harvester as defined in claim 8, wherein the piezoelectric transducer comprises a beam and extends from the base to a free end that operates within the magnetic field.

13. A vibrational energy harvester as defined in claim 8, wherein the piezoelectric transducer has a unimorph zigzag geometry comprising a plurality of beams arranged parallel with one another with a gap defined between adjacent beams, each one of the beams being connected to an adjacent one of the beams by a connecting portion located at an end of each of the connected beams.

14. A vibrational energy harvester as defined in claim 8, wherein the piezoelectric transducer extends between a first end at said base and a second end and includes a layer of piezoelectric material, at least a portion of the piezoelectric transducer being arranged in a back and forth pattern between the first and second ends.

15. A method comprising the steps of:
   providing a piezoelectric transducer having a geometry with an associated power output over a range of input frequencies; and
   inducing non-linear force-deflection behavior in the piezoelectric transducer, thereby increasing the power output of the transducer over the range of input frequencies.

16. The method of claim 15, wherein the step of inducing is performed by providing a magnetic force that acts on the transducer in such a way that the magnitude of the magnetic force varies with the amount of deflection of the transducer.

17. An implantable biomedical device, comprising a piezoelectric energy harvester having a piezoelectric transducer configured to exhibit non-linear force-deflection behavior.

18. An implantable biomedical device as defined in claim 17, wherein the energy harvester is responsive to a heartbeat waveform.

19. An implantable biomedical device as defined in claim 18, wherein the piezoelectric energy harvester is bi-stable and generates greater than 3 µW of power at all heart rates ranging from 7 beats per minute to 700 beats per minute.

20. A wireless monitoring device adapted for attachment to a structure to be monitored, the monitoring device being powered by a piezoelectric energy harvester configured to harvest vibrational energy from the structure and comprising a piezoelectric transducer having a layer of piezoelectric material, wherein:
   at least a portion of the piezoelectric transducer is configured to undergo mechanical strain in response to movement of the energy harvester and is arranged in a back and forth pattern between first and second ends of the transducer;
   the piezoelectric transducer exhibits non-linear behavior; or
   at least a portion of the piezoelectric transducer is configured to undergo mechanical strain in response to movement of the energy harvester and is arranged in a back and forth pattern between first and second ends of the transducer, and the piezoelectric transducer exhibits non-linear force-deflection behavior.

* * * * *